United States Patent [19]

Blount

[11] 4,096,118

[45] Jun. 20, 1978

[54] PROCESS FOR THE PRODUCTION OF AMINO SILICATE COMPOUNDS AND THEIR RESINOUS PRODUCTS

[76] Inventor: David H. Blount, 5450 Lea St., San Diego, Calif. 92105

[21] Appl. No.: 840,557

[22] Filed: Oct. 11, 1977

[51] Int. Cl.² ............................................. C08G 77/04
[52] U.S. Cl. .......................... 260/46.5 E; 260/46.5 R; 260/301; 260/448.2 E; 260/448.2 N; 260/448.8 R; 544/196; 260/347.8
[58] Field of Search ................ 260/448.2 E, 448.2 N, 260/448.8 R, 46.5 E, 46.5 R, 249.5, 248 R, 243 R, 243 A, 347.8, 348 SC

[56] References Cited

U.S. PATENT DOCUMENTS 4,069,391  1/1978  Blount ..................... 260/448.8 R X Primary Examiner—Paul F. Shaver

[57] ABSTRACT

Amino silicate compounds are produced by the chemical reaction of a fine granular silica with amino compounds in the presence of a strong alkali at a suitably elevated temperature, and then the amino silicate compounds are reacted with aldehydes to produce resinous products.

12 Claims, No Drawings

PROCESS FOR THE PRODUCTION OF AMINO SILICATE COMPOUNDS AND THEIR RESINOUS PRODUCTS

BACKGROUND OF THE INVENTION

This invention relates in general to a process for the production of amino silicate compounds and their resinous products.

The silica ($SiO_2$) may be produced by any of the well known methods. It is preferred that the silica be in the form of fine granules or powder.

Amino slicate compounds may be produced by the process in U.S. Pat. No. 4,033,935, inventor: David H. Blount; in this process a hydrated silica ($SiO_2 \cdot x\, H_2O$), in the form of silicic acid is reacted with an amino compound. In this invention the amino compound is reacted with silica ($SiO_2$). Silica is not readily soluble in an alkali aqueous solution as is a hydrated silica. Silica requires a much stronger alkali catalyst to promote the chemical reaction of silica with an amino compound.

Amino silicate compounds are useful as intermediates for the production of other compounds by further suitable reactions. Typically, they may be used in the production of prepolymers, polymers and resins, as an additive or a reactant. Also, they may be used in coating agents, adhesives, impregnants, molding powders, paints, varnishes, laminates, or their manufacture, and may be reacted with other polymerizing compounds.

The poly (aldehyde amino silicate) resinous products are useful as coating agents, adhesives, impregnants, molding powders, paints, varnises, laminates or their manufacture, and may be reacted with other polymerizing compounds.

SUMMARY OF THE INVENTION

I have discovered that silica ($SiO_2$) will react chemically with an amino compound in the presence of a suitable alkali catalyst at a temperature just above the melting temperature of the amino compound but below the boiling temperature of the amino compound. The silica will react with the amino compound in the ratio of 1:1 mols, 1:2 mols, or 2:1 mols. It is preferred that the reaction take place in an aqueous solution.

The exact chemical reactions that take place to produce amino silicate compound is not known; typical reactions which are believed to occur take place as follows:

Silica is theorized to react with urea as follows:

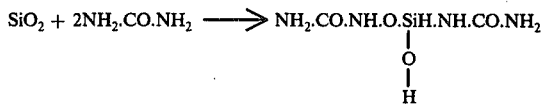

Urea silicate is theorized to react with formaldehyde as follows:

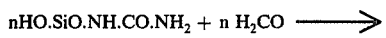

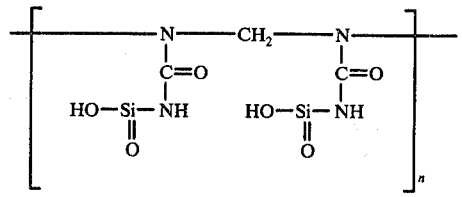

Reactions with other amino compounds are expected to be similar to these, so that the mol ratios of the reactants should be selected accordingly.

DETAILED DESCRIPTION OF THE INVENTION

Any suitable amino compound may be used in my novel process. Typical amino compounds include urea, thiourea, melamine, aniline, quanidine, saccharin, propyl urea, butyl urea, benzene and toluene, sulfonamide, ammeline, dicyandiamide, aliphatic diamine, aromatic diamines, other alkyl-substituted ureas, alkyl-substituted thiourea and mixtures thereof.

Various aldehydes may be used, such as formaldehyde, acetaldehyde, butyaldehyde, chloral, acrolein, furfural and mixtures thereof. The aldehyde ratio may vary from 1:1 to to 5:1 when reacting with an amine silicate, depending on the methyl group desired.

The chemical reaction between silica and an amino compound may take place in a basic pH of 8 to 12, but a pH of 10 to 12 is preferred. The basic catalyst may be alkali metal oxides, alkali metal hydroxides and alkaline earth metal hydroxides. The preferred alkali metal hydroxide is sodium hydroxide. The preferred alkaline earth metal hydroxide is calcium hydroxide. The alkali may act as a catalyst directly, or it may react slightly with one or the other of the primary reactants.

The chemical reaction between an amino silicate compound and an aldehyde may take place in a basic, neutral or acidic pH, but is enhanced by a basic or an acidic pH. The acidic catalysts most commonly used are sodium hydrogen sulfate, sulfuric acid, phosphoric acid, hydrochloric acid, formic acid, acetic acid, and acid esters, such as acid alkyl phosphates. The most common basic catalysts are sodium carbonate, calcium hydroxide, sodium hydroxide, potassium hydroxide, potassium carbonate, ammonia and alkanolamine.

The poly (aldehyde amino silicate) resinous product in the liquid state may be converted to a fully hardened state by prolonged heating. Plasticizers may be used to improve flexibility and adhesiveness. Latent catalysts may be used to catalyze the final conversion of the molding powder from the initial stages of resin formation to the infusible, insoluble product. An excess amount of silica may be used as a filler.

The amino silicate compounds may also form resinous products with acetones, furans, isocyanates, polyisocyantes, epoxy compounds and resins, dicarboxylic acid and anhydrides, halosilicones, and may be copolymerized with unsaturated polymerable organic compounds.

DESCRIPTION OF PREFERRED EMBODIMENTS

The following examples describe in detail certain preferred embodiments of the process of my invention. The preferred processes, of course, may be varied as described above with similar results. Parts and percentages are by weight unless otherwise indicated.

EXAMPLE 1

2 parts by weight of fine granular silica, 2 parts by weight of urea, 1 part by weight of sodium hydroxide flakes and 10 parts by weight of water are mixed then heated to 80° to 100° C while agitating at ambient pressure until the water evaporates. The mixture is then heated to above the melting point of urea but below the boiling point of urea, while agitating for 10 to 30 minutes thereby producing urea silicate, a gray granular compound.

The urea silicate compound is soluble in dilute mineral acids, aldehyde solutions, alcohols, and other organic compounds. The urea silicate compound, when in a solution of dilute mineral acids, may be precipitated out by adding a basic compound until the pH is about 7. It precipitates out as a while granular compound.

EXAMPLE 2

2 parts by weight of fine granular silica, 1 part by weight of urea, 0.5 part by weight of potassium hydroxide and 10 parts by weight of water are mixed then heated to 80° to 100° C while agitating at ambient pressure until the water evaporates. The mixture is then heated to above the melting temperature of urea but below the boiling point for 10 to 30 minutes thereby producing ureas disilicate.

The urea disilicate is soluble in alkali hydroxide, dilute sulfuric acid and other solvents.

EXAMPLE 3

About 1 mol of the urea silicate as produced in Example 1 and 1 mol of formaldehyde in an aqueous solution are mixed then heated to 70° to 110° C while agitating for 20 to 120 mminutes, or until the desired viscosity is reached, thereby producing poly (formaldehyde urea silicate) resinous product.

The resinous product is light gray in color. The liquid resinous product may be used as an adhesive for wood and also may be used as a protective coating for wood. The solid resin may be softened with heat and molded into useful products such as art objects, knobs, etc. The solid resin is soluble in acetic acid and may be used as a varnish or paint to protect wood; it leaves a tough, clear, resinous product on the wood when dry.

EXAMPLE 4

About 1 mol of the urea disilicate as produced in Example 2 and 2 mols of formaldehyde in an aqueous solution are mixed, then an acid catalyst, dilute hydrochloric acid is added until the pH is 4 to 5. The solution is then heated to 70° to 110° C while agitating for 20 to 120 minutes, or until the desired viscosity is obtained, thereby producing poly (urea disilicate) resinous product. The resinous product may be in the form of a thick clear liquid or a while solid. The said solid resinous product may be ground into a molding powder. It may be molded into useful products such as art objects, knobs, etc.

EXAMPLE 5

About 1 mol of silica and 2 mols of urea are mixed in water then sodium hydroxide is added until the pH is 10 to 12. The mixture is then heated while agitating until the water evaporates and then heated to above the melting temperature but below the boiling temperature of the mixture while agitating at ambient pressure for 10 to 30 minutes thereby producing diurea silicate.

About 2 mols of furfural are mixed with one mol of the diurea silicate and heated to just below the boiling temperature of furfural while agitating at ambient pressure for 20 to 120 minutes, until the desired viscosity is obtained, thereby producing poly (furfural diurea silicate) resinous product.

The thick brown poly (furfural diurea silicate) resinous product may be poured into a mold, then an acid such as dilute sulfuric acid is added until the pH is 4 to 5; the resinous product solidifies in a few minutes into hard, tough, useful products such as gears, etc.

EXAMPLE 6

About 2 parts by weight of silica, 1 to 3 parts by weight of urea, and 6 to 10 parts by weight of an aqueous solution containing 37% formaldehyde are mixed. Sodium hydroxide is added until the pH is 10 to 12. The mixture is heated to 70° to 110° C while agitating at ambient pressure for 20 to 120 minutes thereby producing poly (formaldehyde urea silicate) resinous product.

EXAMPLE 7

About 1 mol of fine granular silica and one mol of melamine are mixed in water, then sodium hydroxide is added until the pH is 10 to 12. The mixture is then heated while agitating at ambient pressure until the water evaporates; then the mixture is heated to 70° to 260° C while agitating for 10 to 30 minutes, thereby producing melamine silicate.

The melamine silicate is added to 5 mols of aqueous formaldehyde, heated to 70° to 110° C for 20 to 120 minutes, or until the desired viscosity is reached, thereby producing poly (formaldehyde melamine silicate) resinous product.

EXAMPLE 8

2 parts by weight of fine granular silica, 4 parts by weight of melamine, 10 parts by weight of an aqueous solution containing 37% formaldehyde and 0.5 parts by weight of potassium hydroxide pellets are mixed then heated to 70° to 110° C while agitating at ambient pressure for 20 to 120 minutes thereby producing poly (formaldehyde melamine silicate) resinous product.

EXAMPLE 9

About 1 mol of fine granular silica and 1 mol of thiourea are mixed in water, then sodium hydroxide is added until the pH is 10 to 12. The mixture is heated to 70° to 110° C while agitating at ambient pressure until the water has evaporated; the heating is continued at a temperature just above the melting temperature but below the boiling temperature of thiourea while agitating for 10 to 30 minutes thereby producing thiourea silicate.

About 1 mol of the thiourea is mixed with 1 mol of acetoaldehyde in water. The mixture is then heated to 70° to 110° C while agitating for 20 to 120 minutes or until the desired viscosity is reached, thereby producing poly (acetoaldehyde thiourea silicate) resinous product.

The said resinous product is soluble in acetic acid and may be used as a protective coating on wood.

EXAMPLE 10

2 parts of weight of fine granulr silica, 3 parts by weight of dicyandiamide and 10 parts by weight of water are mixed, then sodium hydroxide is added until the pH is 10 to 12. The mixture is then heated to 70° to 110° C while agitating until the water evaporates. The mixture is then heated to above the melting point but below the boiling point of dicyandiamide while agitating for 10 to 30 minutes thereby producing dicyandiamide silicate.

One mol of dicyandiamide silicate and 2 mols of formaldehyde in an aqueous solution are mixed, then sodium hydrogen sulfate is added until the pH is 4 to 5. The mixture is then heated to 70° to 110° C while agitating for 20 to 120 minutes thereby producing poly (formaldehyde dicyandiamide silicate) resinous product.

The said resinous product may be used as a molding powder with about 10% hexamethylene tetramine added to the molding powder. The molding powder is softened by heating then molded into useful products.

EXAMPLE 11

One mol of dicyandiamide silicate as produced in Example 10 and 2 mols of acrolein are mixed in a closed system then heated to just below the boiling point of acrolein while agitating for 20 to 120 minutes or until the desired viscosity is obtained, thereby producing poly (acrolein dicyandiamide silicate) resinous product.

EXAMPLE 12

About 2 parts by weight of fine granular silica and one part by weight of sodium hydroxide are mixed in 10 parts of water then heated to 70° to 100° C for 20 to 30 minutes, then 4 parts by weight of ethylenediamine are added. The mixture is then heated to 80° to 110° C until the water evaporates, then heating is continued at a temperature just below the boiling point of the mixture for 10 to 30 minutes, thereby producing ethylenediamine silicate.

One part by weight of ethylenediamine silicate and 2 parts by weight of crotonaldehyde are mixed then heated to 70° to 110° C while agitating for 20 to 120 minutes or until the desired viscosity is obtained, thereby producing poly (crotonaldehyde ethylenediamine silicate) resinous product.

EXAMPLE 13

One mol of fine granular silica, 1 mol of aniline and 2 mols of formaldehyde in an aqueous solution are mixed, then sodium hydroxide is added until the pH is 10 to 12. The mixture is then heated to 70° to 110° C while agitating for 20 to 120 minutes, or until the desired viscosity is reached, thereby producing poly (formaldehyde aniline silicate) resinous product.

EXAMPLE 14

One mol of fine granular silica and 1 to 2 mols of an arkyl-substituted urea, butyl urea, are mixed in water, then sodium hydroxide is added until the pH is 10 to 12. The mixture is then heated to 70° to 110° C while agitating for 20 to 120 minutes, or until the desired viscosity is reached, thereby producing butyl urea silicate.

One mol of the butyl urea silicate and 2 mols of formaldehyde in an aqueous solution are mixed then heated to 10° to 110° C while agitating at ambient pressure for 20 to 120 minutes or until the desired viscosity is obtained, thereby producing poly (formaldehyde butylurea silicate) resinous product.

EXAMPLE 15

About equal parts by weight of amino silicate as produced in Example 1 and furfuryl alcohol are mixed, then a mineral acid, such as dilute sulfuric acid or hydrochloric acid is added while agitating for a few minutes; the rate of polymerization varies with the pH, thereby producing poly (furfuryl amino silicate) resinous product.

The mixture of amino silicate and furfuryl alcohol may be poured into a mold of useful products such as tool handles, gears, art objects, etc., then acid is added while pouring to produce hard, tough, brown useful products.

EXAMPLE 16

2 mols of fine granular silica, 1 mol of urea, 1 mol of melamine and 5 mols of an aqueous solution of formaldehyde are mixed, then sodium hydroxide is added until the pH is 10 to 12. The mixture is then heated to 70° to 110° C while agitating at ambient pressure for 20 to 120 minutes or until the desired viscosity is obtained, thereby producing a poly (aldehyde amino silicate) resinous product.

Dilute sulfuric acid is added to the poly (aldehyde amino silicate) resinous product until the pH is 4 to 6, then the resinous product is softened with heat and molded into useful products.

EXAMPLE 17

2 mols of fine granular silica, 1 mol of urea, 1 mol of ethylenediamine and 1 to 4 mols of epichlorohydrin are mixed in water, then sodium hydroxide is added until the pH is 10 to 12. The mixture is then heated to 70° to 110° C while agitating at ambient pressure for 20 to 120 minutes or until the desired viscosity is obtained, thereby producing poly (epoxy silicate) resinous product.

The liquid poly (epoxy silicate) resinous product is thermoplastic and may be poured into a mold of useful products such as toys, knobs, handles, etc., then heated for a few minutes, thereby producing tough, solid, useful products.

Although certain specific preferred ingredients and conditions are described in conjunction with the above-detailed description of the Invention and Example, these may be varied and other ingredients may be used, where suitable, with similar results. Other applications, modifications and ramifications of this invention will occur to those skilled in the art upon reading this disclosure. These are intended to be included within the scope o this Invention, as defined in the appended Claims.

I claim:
1. The process for the production of amino silicate compounds by the following steps:
   (a) mixing about 2 parts by weight of fine granular silica ($SiO_2$) and from about 1 to 4 parts by weight of an amino compound, selected from the group consisting of urea, thiourea, alkyl-substituted urea, alkyl-substituted thiourea, melamine, aniline, guanidine, saccharin, benzene sulfonamide, toluene sulfonamide, ammeline, dicyandiamide, aliphatic diamines, aromatic diamines and mixtures thereof, in water;
   (b) adding an alkali catalyst, selected from the group of alkali metal hydroxides consisting of sodium hydroxide and potassium hydroxide, until the pH is 10 to 12;
   (c) heating said mixture to 70° to 110° C while agitating at ambient pressure until the water evaporates, then continue heating at a temperature between the melting and boiling temperature of the amino com- pound while agitating for 10 to 30 minutes, thereby producing an amino silicate compound.

2. The process of claim 1 wherein an aldehyde is reacted chemically with the amino silicate compound to produce a poly (aldehyde amino silicate) resinous product by the following steps:
   (a) one mol of said amino silicate compound is mixed with 1 to 5 mols of an aldehyde, selected from the group consisting of formaldehyde, aqueous solution of formaldehyde, acetoaldehyde, acrolein, crotonaldehyde, chloral, furfural, benzaldehyde, butyraldehyde and mixtures thereof, in an aqueous solution;
   (b) heating said mixture to 7° to 110° C while agitating at ambient pressure for 20 to 120 minutes, thereby
   (c) producing poly (aldehyde amino silicate) resinous product.

3. The process of claim 1 wherein an aldehyde, selected from the group consisting of formaldehyde, aqueous solution of formaldehyde, acetoaldehyde, acrolein, crotonaldehyde, butyraldehyde, chloral, furfural, benzaldehyde and mixture thereof, is added in step (a), thereby producing poly (aldehyde amino silicate) resinous product in step (c).

4. The process of claim 2 wherein an acid catalyst, selected from the group consisting of sodium hydrogen sulfate, sulfuric acid, hydrochloric acid, phosphoric acid, formic acid, acetic acid, acid alkyl phosphates and mixtures thereof, is added in step (a) until the pH is 4 to 6.

5. The process of claim 3 wherein an acid catalyst, selected from the group consisting of sodium hydrogen sulfate, sulfuric acid, hydrochloric acid, phosphoric acid, formic acid, acetic acid, acid alkyl phosphates and mixtures thereof, is added in step (c).

6. The process of claim 4 wherein an alkali catalyst, selected from the group consisting of sodium carbonate, sodium silicate, potassium carbonate, sodium hydroxide, potassium hydroxide, calcium hydroxide, ammonia, alkanolamine, and mixtures thereof is added to the poly (aldehyde aino silicate) resinous product to adjust the pH of 8 to 10.

7. The process of claim 1 wherein silica is reacted with amino compound in the ratio of 2 to 1 mols, thereby producing an amino disilicate compound.

8. The process of claim 1 wherein additional steps are taken wherein the amino silicate compound is mixed with about equal parts by weight of furfuryl alcohol, then the pH is adjusted to a pH of 4 to 6 with a mineral acid while agitating, thereby producing poly (furfuryl aino silicate) resinous product.

9. The process of claim 1 wherein 1 or 2 mols of epichlorohydrin per mol of the amino compound is added in step (a), thereby producing poly (epoxy silicate) resinous product in step (c).

10. The product, amino silicate, as produced by the process of claim 1.

11. The product, poly (aldehyde amino silicate) resinous product, as produced by the method of claim 2.

12. The product, poly (epoxy silicate) resinous product, as produced by the method of claim 9.

* * * * *